US012565631B2

(12) United States Patent
McGibbon et al.

(10) Patent No.: US 12,565,631 B2
(45) Date of Patent: Mar. 3, 2026

(54) BREWERY AND STEAM VENT ODOR CONTROL SYSTEM

(71) Applicant: Simple Solutions Distributing, LLC, West Milford, NJ (US)

(72) Inventors: Andrew McGibbon, West Milford, NJ (US); Louis John Pagano, West Milford, NJ (US)

(73) Assignee: Simple Solutions Distributing, LLC, West Milford, NJ (US)

( * ) Notice: Subject to any disclaimer, the term of this patent is extended or adjusted under 35 U.S.C. 154(b) by 688 days.

(21) Appl. No.: 17/930,699

(22) Filed: Sep. 8, 2022

(65) Prior Publication Data

US 2023/0074097 A1 Mar. 9, 2023

Related U.S. Application Data

(60) Provisional application No. 63/261,015, filed on Sep. 8, 2021.

(51) Int. Cl.
| | |
|---|---|
| *C12H 1/07* | (2006.01) |
| *A61L 9/14* | (2006.01) |
| *C12G 3/02* | (2019.01) |

(52) U.S. Cl.
CPC .............. *C12H 1/063* (2013.01); *A61L 9/145* (2013.01); *C12G 3/02* (2013.01); *A61L 2209/134* (2013.01); *A61L 2209/14* (2013.01); *A61L 2209/21* (2013.01)

(58) Field of Classification Search
CPC ... C12H 1/063; A61L 9/145; A61L 2209/134; A61L 2209/14; A61L 2209/21; C12G 3/02; B01D 2257/90; B01D 2258/0275
See application file for complete search history.

(56) References Cited

U.S. PATENT DOCUMENTS

| | | | | |
|---|---|---|---|---|
| 3,115,299 | A | * 12/1963 | Goettl | .................... F24F 13/10 |
| | | | | 415/156 |
| 4,376,109 | A | 3/1983 | Wolter et al. | |
| 5,476,634 | A | * 12/1995 | Bridges | .................... A61L 2/04 |
| | | | | 422/26 |

(Continued)

FOREIGN PATENT DOCUMENTS

| | | |
|---|---|---|
| CN | 107349769 A | 11/2017 |
| CN | 112728663 A | 4/2021 |

(Continued)

*Primary Examiner* — Maris R Kessel
*Assistant Examiner* — Nebyate Seged
(74) *Attorney, Agent, or Firm* — Aura IP Law, PC

(57) ABSTRACT
The invention disclosed herein relates to an odor control system including features to allow a media scrubber to function to treat a humid, or saturated, or superheated exhaust stream. In some embodiments, the system disclosed herein can capture a humid, or saturated, or superheated exhaust stream, such as from a kettle vent, and dilute the exhaust with fresh air to lower the temperature of the combined air flow below its dew point. Water is drained from the system as it condenses in the system. The combined air flow can be further diluted and/or treated according to embodiments disclosed herein such that the exhaust stream, after having excess water removed, will have a relative humidity (RH) value enabling it to be run through a media scrubber.

20 Claims, 11 Drawing Sheets

(56) References Cited

U.S. PATENT DOCUMENTS

| | | | | |
|---|---|---|---|---|
| 5,836,297 A | * | 11/1998 | Kawasaki | ............... F24C 15/20 |
| | | | | 126/300 |
| 2005/0058571 A1 | * | 3/2005 | Yin | ........................... A61L 2/26 |
| | | | | 422/26 |
| 2015/0352486 A1 | * | 12/2015 | Xu | ....................... B01D 53/502 |
| | | | | 422/168 |
| 2019/0022579 A1 | * | 1/2019 | Cowles | .............. B01D 53/0446 |
| 2020/0018500 A1 | | 1/2020 | Jeong et al. | |

FOREIGN PATENT DOCUMENTS

| | | | |
|---|---|---|---|
| KR | 200179071 Y1 | 4/2000 | |
| WO | 2009142418 A2 | 11/2009 | |
| WO | 2014043782 A1 | 3/2014 | |

* cited by examiner

70

70A

70B

70C

BREWERY AND STEAM VENT ODOR CONTROL SYSTEM

CROSS REFERENCE TO RELATED APPLICATIONS

This application claims priority to U.S. Provisional Application Ser. No. 63/261,015 filed Sep. 8, 2021, which is hereby incorporated by reference in its entirety.

TECHNICAL FIELD OF THE INVENTION

Embodiments of the invention disclosed herein relate generally to odor control systems. More particularly, embodiments of the invention relate to a system for adjusting relative humidity of an exhaust flow to permit odor treatment thereof.

BACKGROUND TO THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the invention disclosed herein, or any embodiments thereof, to anything stated or implied therein or inferred thereupon.

Odorous gases can often be an unwanted byproduct of certain processes that need to be controlled. For example, hydrogen sulfide ($H_2S$) and dimethyl sulfide ($C_2H_6S$, DMS) are gases that are a biproduct of the beer brewing process. These gasses can be released into the atmosphere during the wort boiling process. For example, these gasses can exit the beer kettle through the vent and can be carried out in the steam.

While the kettles are boiling, the exhaust stream is saturated with water, making the exhaust stream unable to run through an odor scrubbing media, such as an activated carbon filter, for example, or other medias depending upon the compounds to be removed. The amount of water in the steam and the quantities of $H_2S$ and DMS will vary depending on kettle size, number of kettles in system, boil time and the like.

As can be seen, there is a need for a cost-effective system for controlling odor from beer kettle vents during a brewing process.

SUMMARY OF THE INVENTION

Embodiments of the invention disclosed herein provide an odor control system for treating a humid, or saturated, or super saturated, and/or super-heated exhaust stream. In some embodiments, an odor control system for allowing a media scrubber to function to treat a humid, or saturated, or superheated exhaust stream is disclosed. In some embodiments, the system can capture a humid, or saturated, or superheated exhaust stream, such as from a kettle vent, and dilute the exhaust with fresh air to lower the temperature of the combined air flow below its dew point. In some embodiments, water is drained from the system as it condenses in the system. In some embodiments, the combined air flow can be further diluted and/or treated according to embodiments disclosed herein such that the exhaust stream, after having excess water removed, will have a relative humidity (RH) value enabling it to be run through a media scrubber.

In some embodiments, the odor control system includes an air admittance tee operable to receive a humid, saturated, super saturated, and/or superheated exhaust stream and a fresh air flow to create a combined outflow that is cooled and a treatment zone operable to treat the combined outflow. In some embodiments, the odor control system disclosed herein includes an air admittance tee operable to receive an exhaust flow; a damper in the air admittance tee permitting an air flow to enter the air admittance tee and mix with the exhaust flow as the exhaust flow moves through the tee to create a combined outflow that is cooled; a first pipe connecting an outlet of the air admittance tee with a treatment zone operable to treat the combined outflow. In some embodiments, the treatment zone includes a demister, a media scrubber and/or a blower.

In some embodiments, the invention provides an odor control system comprising an air admittance tee operable to receive an exhaust flow; a damper in the air admittance tee permitting an air flow to enter the air admittance tee and mix with the exhaust flow as the exhaust flow moves through the tee to create a combined outflow that is cooled; a first pipe connecting an outlet of the air admittance tee with a demister; an air admittance lateral, communicating with the first pipe, operable to permit an external air flow to move into the first pipe to mix with the combined outflow before entering the demister; a damper in the air admittance lateral to regulate a volume of the external air flow; and a second pipe connecting an outlet of the demister with a media scrubber having an adsorbent material. In some embodiments, the system further includes a blower, wherein the blower moves an outflow through the media scrubber by either pushing the outflow through the media scrubber in the instance where the blower is upstream of the media scrubber or pulls the outflow through the media scrubber in the instance where the blower is downstream of the media scrubber.

In some embodiments, the invention provides an odor control system comprising an air admittance tee operable to receive an exhaust flow; a vent in the air admittance tee, the vent permitting escape of the exhaust flow therethrough without the exhaust flow moving through the odor control system; a first valve in the vent, the valve operable to open and close the vent; a damper in the air admittance tee permitting a first external air flow to enter the air admittance tee and mix with the exhaust flow as the exhaust flow moves through the tee to create a combined outflow that is cooled; a first pipe connecting an outlet of the air admittance tee with a demister; a first drain in the first pipe; an air admittance lateral, communicating with the first pipe, operable to permit a second external air flow to move into the first pipe to mix with the combined outflow before entering the demister; a second damper in the air admittance lateral operable to regulate a volume of the external air flow; a second pipe connecting an outlet of the demister with a pressure blower; and a second drain in the second pipe, wherein the pressure blower moves an outflow through a media scrubber having an adsorbent material.

In some embodiments, an odor control system is disclosed. In some embodiments, the odor control system includes an air admittance tee operable to receive a superheated exhaust stream and a fresh air flow to create a combined outflow that is below the dew point and a treatment zone operable to treat the combined outflow. In some embodiments, the system further includes a demister downstream of the air admittance tee and a first pipe connecting the air admittance tee to the demister. In some embodiments, the system further includes a first water drain in the first pipe. In some embodiments, the system further includes an air admittance lateral operable to permit an external air flow to move into the first pipe to mix with the combined outflow before entering the demister. In some embodiments, the system further includes a damper in the air admittance lateral for regulating an amount of the external air flow moving into the first pipe. In some embodiments, the system further includes a vent in the air admittance tee, the vent permitting escape of the exhaust flow therethrough without the exhaust flow moving through the odor control system and a valve in the vent, the valve operable to open and close the vent. In some embodiments, the valve of the air admittance tee is a barometric valve operable to regulate a volume of the air flow therethrough.

In some embodiments, the treatment zone includes a media scrubber having an adsorbent or an oxidizer media disposed therein. In some embodiments, the system further includes the treatment zone further includes an air admittance lateral having a damper operable to permit an external air flow to move through the treatment zone. In some embodiments, the treatment zone includes a blower for facilitating air movement in the system. In some embodiments, the system further includes an air box disposed about the blower, wherein a vacuum is pulled through the air box during operation of the blower.

In some embodiments, the system further includes a pressure gauge disposed on the media scrubber, the pressure gauge measuring a differential pressure through the media, wherein the differential pressure being above a predetermined limit indicates a need to open the damper of the air admittance lateral to permit the external air flow to dry the media. In some embodiments, the system further includes a water drain in the treatment zone. In some embodiments, the system further includes one or more sensors disposed in the system, the one or more sensors operable to measure at least one of a fluid flow, a temperature and a relative humidity.

In some embodiments an odor control system is disclosed, wherein the system includes an air admittance tee operable to receive an exhaust flow; a damper in the air admittance tee permitting an air flow to enter the air admittance tee and mix with the exhaust flow as the exhaust flow moves through the tee to create a combined outflow; a first pipe connecting an outlet of the air admittance tee with a demister; an air admittance lateral, communicating with the first pipe, operable to permit an external air flow to move into the first pipe to mix with the combined outflow before entering the demister; a damper in the air admittance lateral to regulate a volume of the external air flow; and a second pipe connecting an outlet of the demister with a blower, wherein the blower moves an outflow through a media scrubber having an adsorbent or an oxidizer material. In some embodiments, the system further includes a first water drain in the first pipe and a second water drain in the second pipe. In some embodiments, the system further includes a vent in the air admittance tee, the vent permitting escape of the exhaust flow therethrough without the exhaust flow moving through the odor control system and a valve in the vent, the valve operable to open and close the vent.

In some embodiments, the system further includes a second air admittance lateral in the second pipe, wherein the second air admittance lateral includes a damper operable to permit an external air flow to move through the media scrubber; and a pressure gauge disposed on the media scrubber, the pressure gauge measuring a differential pressure through the media, wherein the differential pressure being above a predetermined limit indicates a need to open the damper of the air admittance lateral to permit the external air flow to dry the media. In some embodiments, the adsorbent media includes activated carbon or oxidizers.

In some embodiments, on odor control system is disclosed wherein the odor control system includes an air admittance tee operable to receive an exhaust flow; a vent in the air admittance tee, the vent permitting escape of the exhaust flow therethrough without the exhaust flow moving through the odor control system; a first valve in the vent, the valve operable to open and close the vent; a first damper in the air admittance tee permitting a first external air flow to enter the air admittance tee and mix with the exhaust flow as the exhaust flow moves through the tee to create a combined outflow; a first pipe connecting an outlet of the air admittance tee with a demister; a first drain in the first pipe; an air admittance lateral, communicating with the first pipe, operable to permit a second external air flow to move into the first pipe to mix with the combined outflow before entering the demister; a second damper in the air admittance lateral operable to regulate a volume of the external air flow; a media scrubber having an adsorbent material; and a pressure blower, wherein the pressure blower moves an outflow through the media scrubber. In some embodiments, the system further includes a second air admittance lateral prior to the media scrubber, wherein the second air admittance lateral includes a damper operable to permit an external air flow to move through the media scrubber. In some embodiments, the damper of the air admittance tee is a barometric valve operable to regulate a volume of the air flow therethrough.

Methods of treating a humid or saturated or super saturated or superheated exhaust stream, such as to remove odors and/or contaminants using the systems described herein are also disclosed herein.

These and other features, aspects and advantages of the invention will become better understood with reference to the following drawings, description and claims.

BRIEF DESCRIPTION OF THE DRAWINGS

Some embodiments of the invention disclosed herein are illustrated as an example and are not limited by the figures of the accompanying drawings, in which like references may indicate similar elements.

Figure 1:
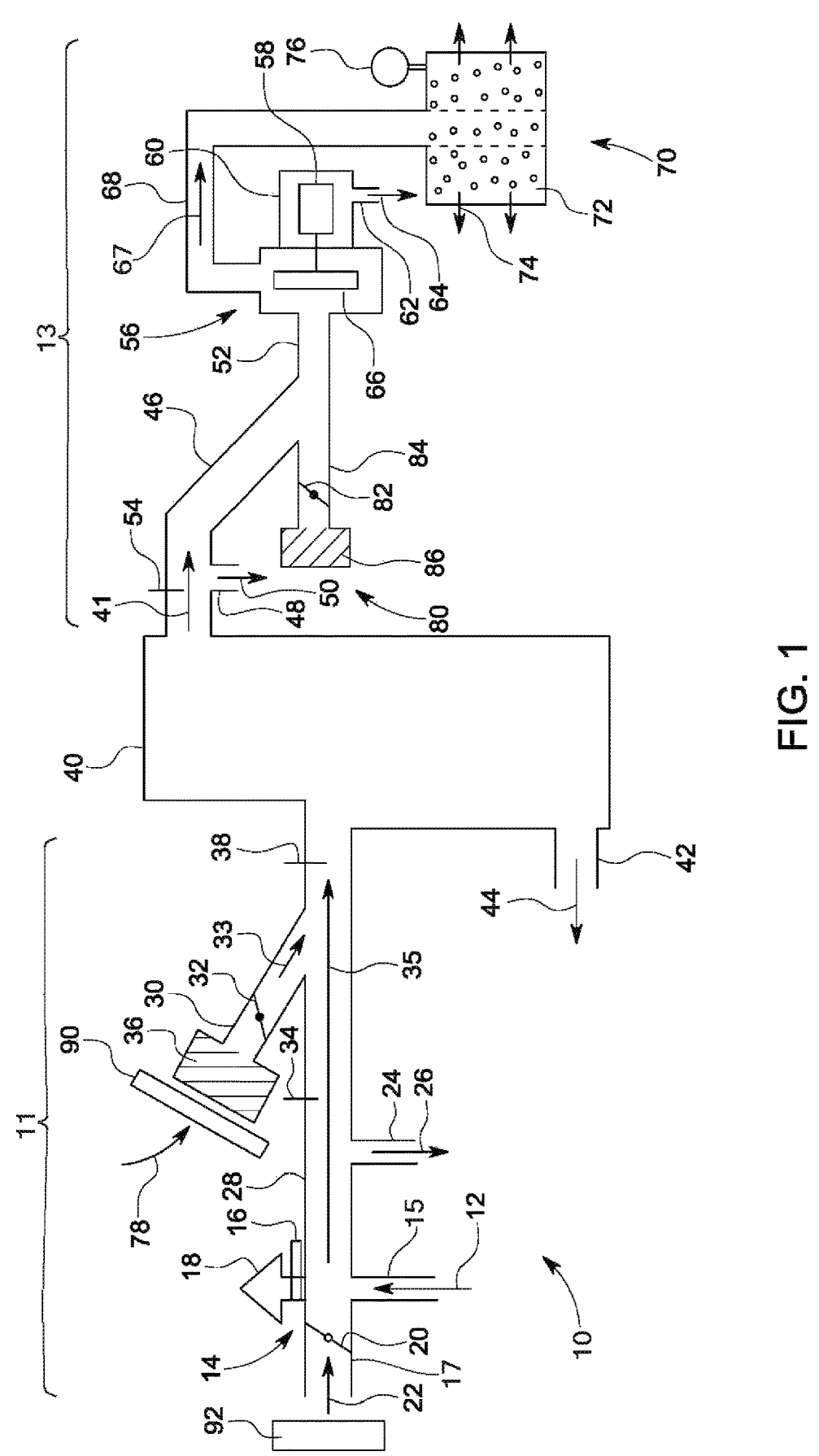
FIG. 1 is a schematic representation of an odor control system according to an exemplary embodiment of the invention described herein.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILS OF THE INVENTION

Broadly, embodiments of the invention described herein provide an odor control system including features to allow a media scrubber to function to treat a humid exhaust stream, or a steam exhaust, or a saturated or super saturated exhaust, or a super-heated exhaust. In some embodiments, the media scrubber is, for example, but not limited to, an activated carbon scrubber, a standard carbon scrubber, an updraft scrubber, a downdraft scrubber, a radial scrubber, an inline scrubber, and the like. In some embodiments, the system disclosed herein captures steam and/or saturated exhaust from exhaust vents and dilutes the captured exhaust with outside air to bring the temperature of the exhaust stream below its dew point prior to being treated.

In some embodiments, water is drained as it condenses in the duct work. In some embodiments, the system includes one or more lateral air bleads, wherein the exhaust stream is further diluted and additional water drained as it condenses. In some embodiments, the exhaust stream, after having the temperature lowered and excess water removed by the system has a relative humidity (RH) value of less than about 70%, less than about 75%, less than about 80%, less than about 85%, less than about 90%, or less than about 91%, or less than about 92%, or less than about 93%, or less than about 94%, or less than about 95%, or less than about 96%, or less than about 97%, or less than about 98%, or less than about 99%, enabling it to be run thru a media scrubber.

In some embodiments, the exhaust stream is treated once it has been diluted, and/or temperature lowered, and/or liquid removed. For example, in some embodiments, the diluted exhaust stream enters a demister assembly, such as, for example, but not limited to, a mesh demister, vane-type demister, cyclonic demister, coalescer and/or fiber-bed demister, and the like, to further lower the temperature of and further remove liquid from the exhaust stream. The demister assembly separates any water that has dropped out of gas phase. In some embodiments, the exhaust stream exiting the demister assembly is run through a duct system that has an additional water drain for capturing and removing any water that condenses out of gas phase after the demister assembly.

In some embodiments, the system includes a blower motor to push or pull the exhaust stream through the system. For example, in some embodiments, the system includes a blower motor upstream of a media scrubber and the exhaust stream is pushed through the media scrubber. In some embodiments, the system includes a blower motor downstream of a media scrubber and the exhaust stream is pulled through the media scrubber. The blower motor can vary in size depending on the size of the system.

The media scrubber can vary in size depending on the application. In some embodiments, the media scrubber is a carbon scrubber, an activated carbon scrubber, an updraft scrubber, a downdraft scrubber, a radial scrubber, an inline scrubber, and the like.

In some embodiments, the water separated out of the exhaust stream is drained into a one or more plumbing drains throughout the system. In some embodiments, the drained water is treated, for example, the drained water can be run through an acid neutralizing media, such as, but not limited to, a limestone bed, to neutralize any acids that can be dissolved in the separated water, such as, but not limited to, sulfuric acid.

As used herein, a "kettle" refers to any container or device for boiling liquids.

As used herein, the term "relative humidity" is used to refer to steam mixed with air below the saturation temperature (e.g., 1 bar, 99.6 degrees Celsius). Relative humidity describes how far the air is from saturation. Relative humidity is a ratio that compares the amount of water vapor in the air with the amount of water vapor that would be present in the air at saturation. In other words, "relative humidity" is water vapor content/water vapor capacity. Relative humidity is provided as a percentage: the amount of water vapor is expressed as a percent of saturation. For example, at 25 degrees Celsius and 1 atmospheric pressure, the corresponding specific maximum humidity is about 3% although the relative humidity is at 100%.

A "humid exhaust stream" as used herein is one having a relative humidity above of about 80%, about 85%, about 90%, about 91%, about 92%, about 93%, about 94%, about 95%, about 96%, about 97%, about 98%, about 99%, or about 100%.

As used herein, "steam," refers to vaporized water. Steam is a chemically pure, invisible gas (not a mist) which at standard atmospheric pressure (1 atmosphere) has a temperature greater than 100 degrees Celsius and occupies about 1,600 times, or more, the volume of the same mass of liquid water. Steam can be much hotter than the boiling point of water where gas first starts to form. Steam can be saturated or superheated.

As used herein, the term "saturated" refers to steam at the boiling temperature (which depends on the pressure). At sea level and one atmosphere pressure (101 KPa) steam boils at 100 degrees Celsius (212 degrees Fahrenheit) which is called the saturated steam temperature for this pressure. Saturated steam has a 100% relative humidity. Condensation of steam to water begins to occur when the temperature is lowered.

As used herein, the term "superheated" refers to steam above the boiling temperature (which depends on pressure). The characteristics of the relative humidity scale change drastically in the super heat area. Below 100° C./212° F. it is possible to achieve 100% relative humidity at any temperature. Above 100° C./212° F. (superheated state) the maximum possible relative humidity plunges rapidly as the temperature increases. Pure steam (100° C./212° F. dew point) will register only 20% on the relative humidity scale at 150° C./302° F. At 175° C./347° F. the maximum possible relative humidity is only 10%. At 200° C./392° F., maximum relative humidity is only 5.9% and at 370° C./698° F., maximum relative humidity is 0.48%. Thus, the maximum relative humidity changes as temperature increases.

As used herein "dew point" refers to the temperature to which air must be cooled to become saturated without changing the pressure. Changing the pressure affects the vapor pressure and therefore the temperature at which saturation occurs. Thus, the dew point temperature is determined by keeping the pressure fixed. Changes in pressure slightly modify the dew point temperature. When the dew point equals the air temperature, the air is "saturated" and the relative humidity is 100%. The closer the dew point is to the air temperature, the closer the air is to saturation. The dew point varies based on outside temperature. Above the dew point, water is still suspended in the air but can be removed. Below the dew point water drops from gas phase to liquid phase and can be separated.

As used herein "specific humidity" (also called the "humidity ratio") is used to refer to the ratio of mass of water vapor to the mass of dry air at high temperatures.

Referring now to FIG. 1, an overview of an exemplary embodiment of a system 10 for odor control as described herein is provided, where details on each component follows with respect to respective detailed drawings. The system 10 includes an air intake zone 11 and a treatment zone 13. In some embodiments, the system 10 further includes an optional demister 40. The air intake zone 11 can receive an exhaust flow 12 into an air admittance tee 14 through an exhaust inlet 15 at one end of the air admittance tee 14. In some embodiments, the exhaust inlet 15 is located at an inferior end of the air admittance tee 14. The exhaust flow 12 can be received from various industrial operations where capture and treatment of the exhaust flow 12 is desired. In some embodiments, the exhaust flow 12 is a humid exhaust flow, or steam exhaust flow, or saturated exhaust flow, or superheated exhaust flow, for example, from a kettle used to boil liquid. In some embodiments, the exhaust flow is from a brewery, restaurant, large kitchen, food processing, food packaging, and/or chemical processing operation. For example, in some embodiments, the exhaust flow is from one or more kettles and/or whirlpools of a brewery operation.

The system 10 is configured to receive a fresh air flow 22 into the air admittance tee 14 through a fresh air inlet 17 in the air admittance tee 14. In some embodiments, the fresh air inlet 17 is perpendicular to the exhaust inlet 15. In some embodiments, the exhaust flow 12 is a humid exhaust flow, or a steam exhaust flow, or a saturated exhaust flow, or a superheated exhaust flow and the fresh air flow 22 cools the exhaust flow 12 resulting in the temperature of the combined outflow 35 being lowered below its dew point and water vapor condensing into a liquid phase. Such condensation occurs in the intake pipe 28 and can be drained as a first wastewater flow 26 via a first drain 24 located in the intake pipe 28. In some embodiments, the wastewater can be treated downstream of the first drain 24.

In some embodiments, the air admittance tee 14 includes an exhaust vent 18, wherein the exhaust flow 12 can be diverted out of the air admittance tee 14 through the exhaust vent 18, typically positioned on the air admittance tee 14 superior to the exhaust inlet 15. The diverted exhaust flow occurs when exhaust valve 16 is in an open position. Such a configuration provides the option to bypass the downstream treatment process. When the exhaust valve 16 is closed, the exhaust flow 12 is mixed with fresh air flow 22 resulting in a cooled combined outflow 35 and creating condensation in the intake pipe 28 that is drained as a first wastewater flow 26 via a first drain 24 in the intake pipe 28.

In some embodiments, one or more additional fresh air flows 33 can be optionally added to the cooled combined outflow 35 via one or more air admittance laterals 30 connected to the intake pipe 28. The one or more air admittance laterals 30 can include an air admittance lateral damper 32, whereby the additional fresh air flow 33 occurs when the air admittance lateral damper 32 is at least partially open. Optionally, the air admittance lateral 30 includes a filter element 36 through which the additional fresh air flow 33 can pass prior to entry into the air admittance lateral 30.

In some embodiments, downstream of the air admittance tee 14 and the one or more optional air admittance laterals 30 is a demister 40, as may be known in the art, that further lowers the temperature of the combined outflow 35 to below dew point and removes liquid water from the combined outflow 35. In some embodiments, a demister drain 42 in the demister 40 can permit a second wastewater flow 44 to exit the demister 40. A demister outflow 41 from the demister 40 can pass through demister outlet pipe 46. In some embodiments, demister outlet pipe 46 can include a drain 48 for permitting a third wastewater flow 50 to exit the demister outlet pipe 46.

In some embodiments, the wastewater flows 26, 44, 50 can optionally be treated. For example, in some embodiments, the wastewater is acidic and is passed through neutralization media, such as, but not limited to, limestone, to neutralize any acidic components therein.

In some embodiments, the demister outflow 41 has a relative humidity that is sufficient to be suitable for treatment via a treatment process. For example, in some embodiments, the demister outflow 41 from the demister 40 has a relative humidity of less than about 70%, less than about 75%, less than about 80%, less than about 85%, less than about 90%, or less than about 91%, or less than about 92%, or less than about 93%, or less than about 94%, or less than about 95%, or less than about 96%, or less than about 97%, or less than about 98%, or less than about 99%.

In some embodiments, the treatment process can be designed for removal of contaminants in the exhaust flow 12, 35, 41. For example, in a brewery operation, contaminants can include, for example, but not limited to, $H_2S$ and DMS, and the treatment process can include passing the demister outflow 41 through media 72 in a media scrubber 70. Such media can include, for example, but not limited to, activated carbon, ferric hydroxide impregnated clay, an iron EDTA (ethylenediaminetetraacetate) complex, iron sponges, potassium permanganate, impregnated medias, and the like. In some embodiments, the media scrubber is, for example, but not limited to, a standard carbon scrubber, an activated carbon scrubber, an updraft scrubber, a downdraft scrubber, a radial scrubber, an inline scrubber, and the like. In some embodiments, the treated outflow 74 from the media scrubber 70 has a significantly reduced concentration of contaminants. For example, in some embodiments, the concentration of contaminants in treated outflow 74 is below an odor threshold or olfactory detection limit, for example, below 10 ppm, or below 5 ppm, or below 3 ppm, or below 2.5 ppm, or below 2 ppm, or below 1.5 ppm, or below 1 ppm, below 0.5 ppm, below 0.1 ppm, below 0.05 ppm, below 0.01 ppm and/or below detectable levels (such as zero ppm).

In some embodiments, a pressure blower 56 is provided and includes a blower motor 58 to drive a blower 66 and move air flow 12, 35, 41 through the system 10. In some embodiments, pressure blower 56 is positioned in the system such that it pushes air flow air flow 12, 35, 41 through the media scrubber 70. That is, in some embodiments, pressure blower 56 is positioned upstream of media scrubber 70. In some embodiments, pressure blower 56 is positioned in the system such that it pulls air flow air flow 12, 35, 41 through the media scrubber 70. That is, in some embodiments, pressure blower 56 is positioned downstream of media scrubber 70.

In some embodiments, an air box 60 is used to encase the pressure blower 56 and/or the blower motor 58. In some embodiments, a vacuum 64 is applied inside the air box 60 via vacuum tube 62. The vacuum 64 can be used to both remove any leakage from the pressure blower 56 and to provide a cooling fresh air flow over the blower motor 58 to prevent overheating of the pressure blower 56.

In some embodiments, one or more treatment air admittance laterals 84 are provided on an intake side 52 of the pressure blower 56. In some embodiments, the one or more treatment air admittance laterals 84 contain a damper 82 that can be closed. In some embodiments, if the media 72 in the media scrubber 70 becomes saturated and needs a drying air flow, the system 10 can be run (without receiving the exhaust flow 12) with the damper 82 open to permit a fresh air flow 80 to be pushed through the media 72 in the media scrubber 70. Optionally, the one or more treatment air admittance laterals 84 include a filter element 86 through which the additional fresh air flow 80 passes prior to entry into the treatment air admittance lateral 84. Such maintenance operation can be performed periodically or when a pressure provided by a pressure differential gauge 76 is greater than a predetermined limit, where such a pressure can indicate that (1) the media 72 is too wet and needs a drying flow via the treatment air admittance lateral 84, or (2) the media 72 needs replacement. For example, in some embodiments, the media is activated carbon and a pressure increased by about 0.5 inch, or by about 0.75 inch, or by about 1 inch, or by about 1.5 inch, or by about 1.75 inch, or by about 2 inches, or by about 2.25 inches, or by about 2.5 inches, or by about 2.75 inches, or by about 3 inches above the starting pressure is the predetermined limit that indicates a need for maintenance. As would be understood by those of ordinary skill in the art, the pressure increase will vary depending on size of the media bed, the media used, and other similar conditions.

In some embodiments, air flow 12, 22, 35, 41, 67 passes through media inlet pipe 68 into a media scrubber 70.

In some embodiments, various sensors 34, 38, and/or 54 are optionally provided to measure flow, temperature, relative humidity, and the like. The sensors 34, 38, and/or 54 facilitate proper adjustment of dampers 20, 32, and/or 82 to reach a desired relative humidity at various points inside the system 10. For example, in some embodiments, sensors 34, 38, and/or 54 facilitate proper adjustment of dampers 20, 32, and/or 82 to reach a relative humidity that it is suitable for treatment.

In some embodiments, sensors 34, 38, and/or 54 report data to a computing device configured to read measurements from the sensors 34, 38, and/or 54 and to automatically adjust dampers 20, 32, and/or 82, and/or to automatically adjust the speed of the pressure blower 56 so that the treatment is optimized. In some embodiments, sensors 34, 38, and/or 54 are read by a user and dampers 20, 32, 82, and/or the speed of the pressure blower 56 are adjusted manually by the user. In some embodiments, sensors 34, 38, and/or 54 are not included and the system 10 performs successfully with manual adjustment of dampers 20, 32, 82, and/or the speed of the pressure blower 56. In some embodiments, additional sensors are included to facilitate operation of the system 10. Such sensors can, for example, measure contaminant concentrations in the exhaust flow 12 and/or in the outflow 74 from the media scrubber 70 to monitor system effectiveness.

In some embodiments, fresh air flow 22 provided to the air admittance tee 14 passes through an air treatment device 92 prior to entering the air admittance tee 14. In some embodiments, a similar air treatment device 90 is provided at the one or more air admittance laterals 30 to treat the fresh air flow 78 taken into the one or more air admittance laterals

30. In some embodiments, air treatment devices 90 and/or 92 cool and/or dehumidify fresh air flows 22 and/or 78. Although not required, this can be beneficial, for example, when the system 10 is, itself, disposed in a warm and/or humid climate. In some embodiments, the air treatment devices 90 and/or 92 include cooling condensers, Peltier cooling devices, heat exchangers, or the like.

Figure 2:
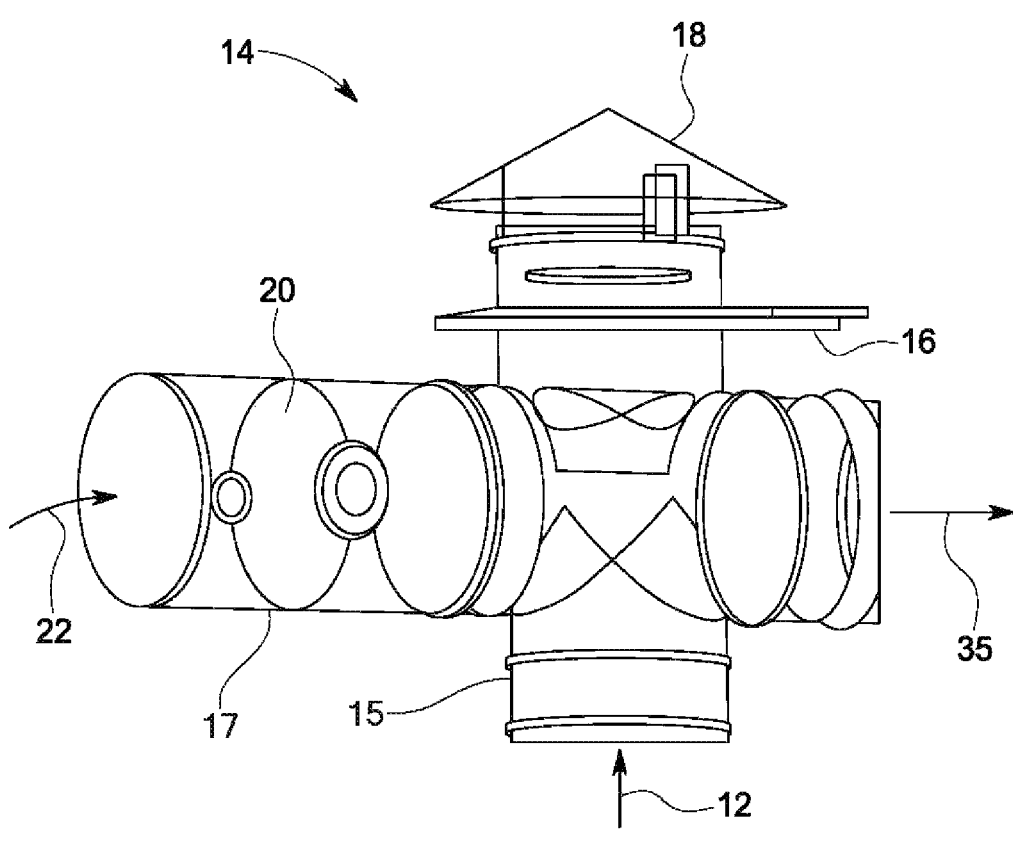
FIG. 2 is a detailed view of an air admittance tee used in the odor control system of FIG. 1.
Figure 3:
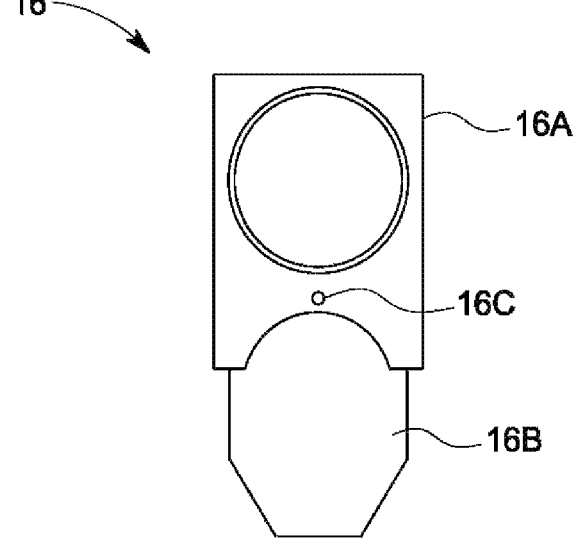
FIG. 3 is a top view of a valve used in the air admittance tee of FIG. 2.

Referring now to FIGS. 2 and 3, along with FIG. 1, the air admittance tee 14 is shown in detail. In some embodiments, exhaust vent 18 is configured as a rain cap to prevent rain from entering the system when exhaust valve 16 is open. Exhaust valve 16 can be designed in any configuration, such as, for example, but not limited to, a gate valve, that allows it to selectively move between an open configuration, permitting exhaust flow 12 to exit via exhaust vent 18, and a closed configuration, directing exhaust flow 12 toward the treatment zone 13. For example, as shown in FIG. 3, in some embodiments, exhaust valve 16 includes a valve base 16A and a sliding member 16B that can slide to cover an opening through the valve base 16A. A retention mechanism 16C can be provided to lock the sliding member 16B in the open or closed configurations. The retention mechanism 16C can be, for example, but not limited to, a thumb screw that can pass through the valve base 16 and engage with the sliding member 16B.

In some embodiments, fresh air intake valve 20 is a barometric valve, configured to automatically open, for example, via a Venturi effect, as air flow moves through the air admittance tee 14 toward the treatment zone 13 to dilute the exhaust flow 12. In some embodiments, fresh air intake damper 20 can be manually adjusted to permit a predetermined fresh air flow 22 to dilute and/or cool exhaust flow 12. In some embodiments, fresh air intake damper 20 is automatically adjusted to permit a predetermined fresh air flow 22 to dilute and/or cool exhaust flow 12.

Figure 4:
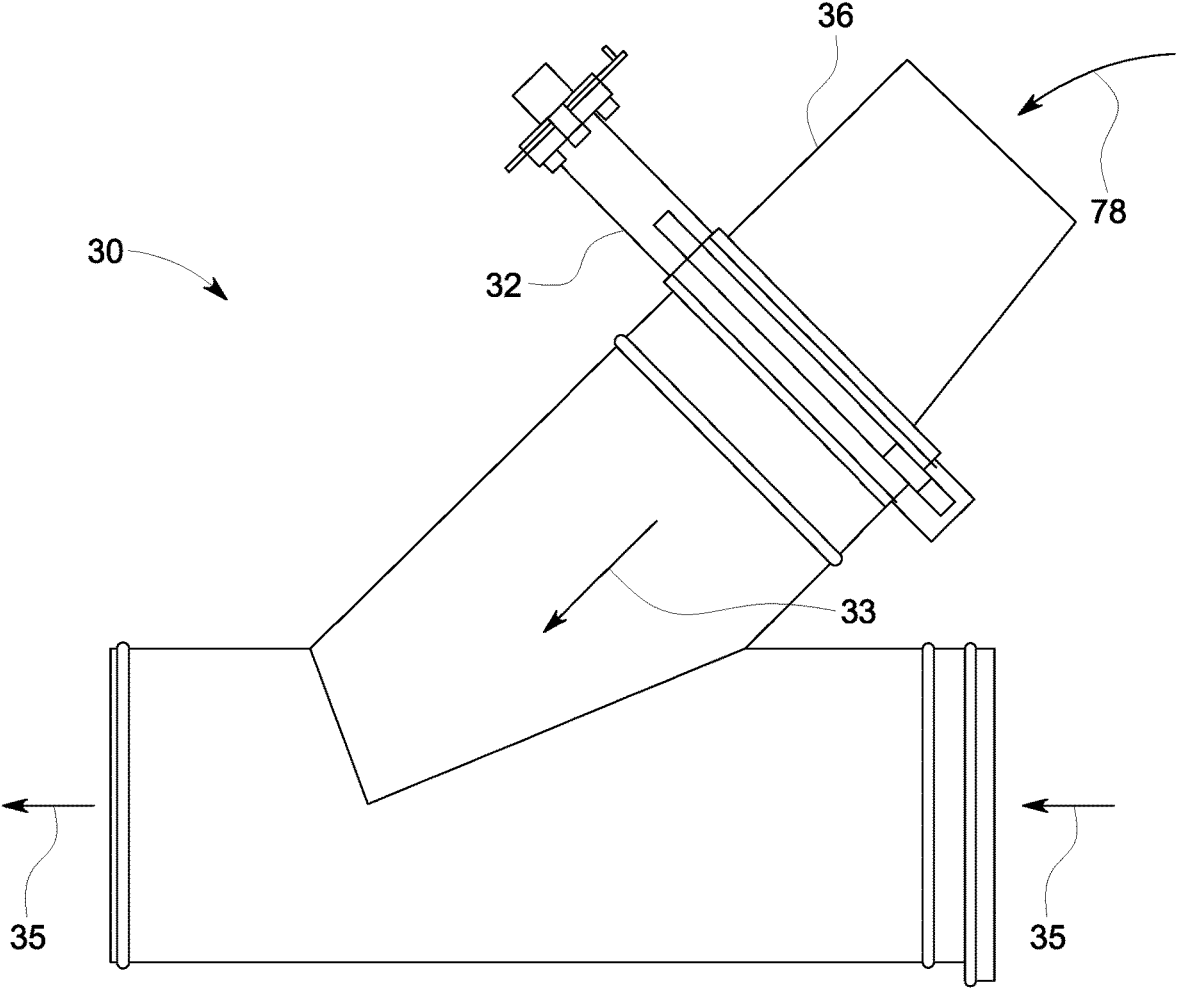
FIG. 4 is a detailed view of a demister air admittance lateral used in the odor control system of FIG. 1.

Referring now to FIG. 4, along with FIG. 1, in some embodiments, air admittance lateral 30 allows fresh air flow 78 to further cool and dilute the cooled, combined outflow 35. Damper 32 can take various forms, for example, but not limited to, a manually actuated butterfly valve. Other valve designs will be apparent to those of skill in the art. Further, as discussed above, the actuation of damper 32 can be performed automatically based on readings from various sensors. Air filter 36 can be, for example, but not limited to, a fabric or woven filter that covers the intake for the fresh air flow 78. In some embodiments, air admittance lateral 30 is formed as a wye, as shown in FIG. 4, although other shapes, such as, but not limited to, a T-shape, can be used. The fresh air flow 78 can be taken into the air admittance lateral 30 due to a Venturi effect caused by the passing of combined outflow 35. Thus, a combination of the speed of the combined outflow 35 (optionally, additionally driven by the pressure blower 56) and the amount damper 32 is opened can determine the amount of the fresh air flow 78 that enters and mixes with combined outflow 35.

Figure 5:
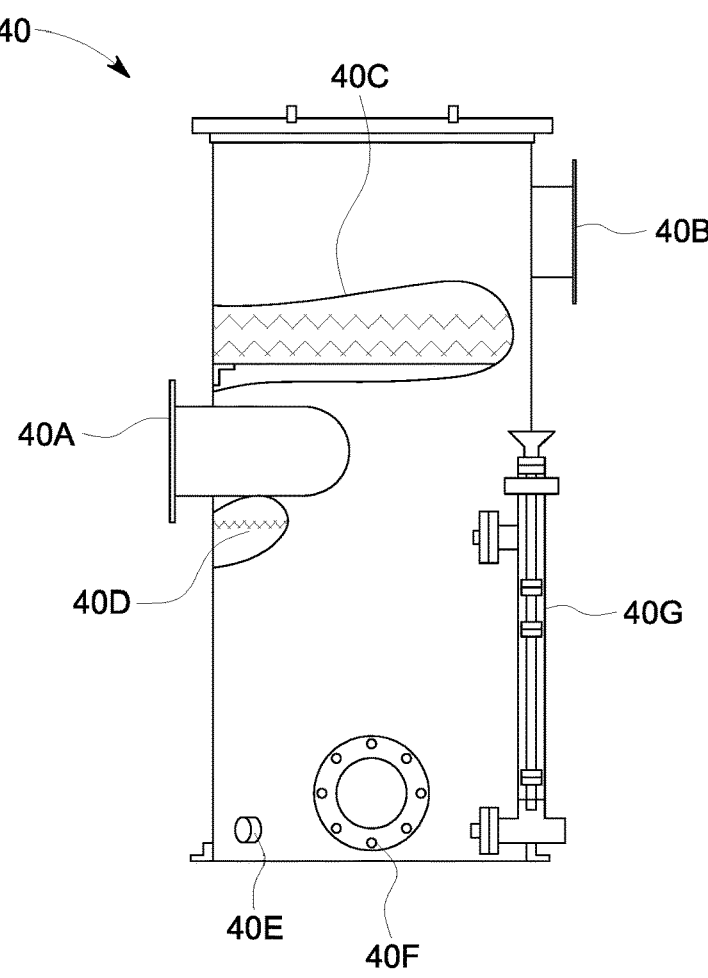
FIG. 5 is a partially cut-away side view of an exemplary demister used in the odor control system of FIG. 1.
Figure 6:
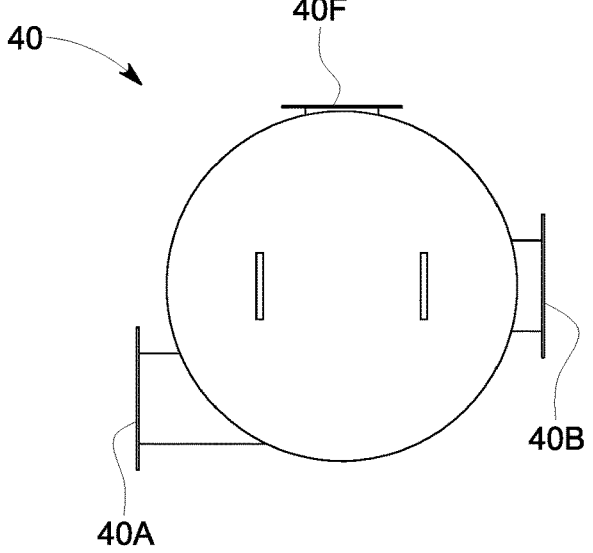
FIG. 6 is a top view of the demister of FIG. 5.

Referring now to FIGS. 5 and 6, along with FIG. 1, in some embodiments, the optional demister 40 receives the combined outflow 35 at an inlet 40A. In some embodiments, the flow through the demister 40 passes through a demister pad 40C before exiting the demister outlet 40B. In some embodiments, the demister 40 includes a drain connection 40E, a cleanout 40F and, optionally, a site glass 40G. In some embodiments, site glass 40G includes switches that activate a warning light if water is not draining, and/or if the demister is clogged and/or frozen. In some embodiments, the demister can trip a switch and pump out water. In some embodiments, the demister can include an emulsion heater if being used in cold weather to prevent freezing. In some embodiments, the demister drain lines can include a heating system to prevent freezing in the cold weather. In some embodiments, the demister pad 40C uses, for example, a fiber reinforced plastic (FRP) support grate. While an exemplary demister is shown, the inclusion of a demister is optional and in some embodiments the system does not include a demister. Various designs, as may be known in the art, can be used in the system 10 disclosed herein, provided that the demister can remove water from the flow to output a flow having a relative humidity suitable for treatment, as discussed above.

Figure 7:
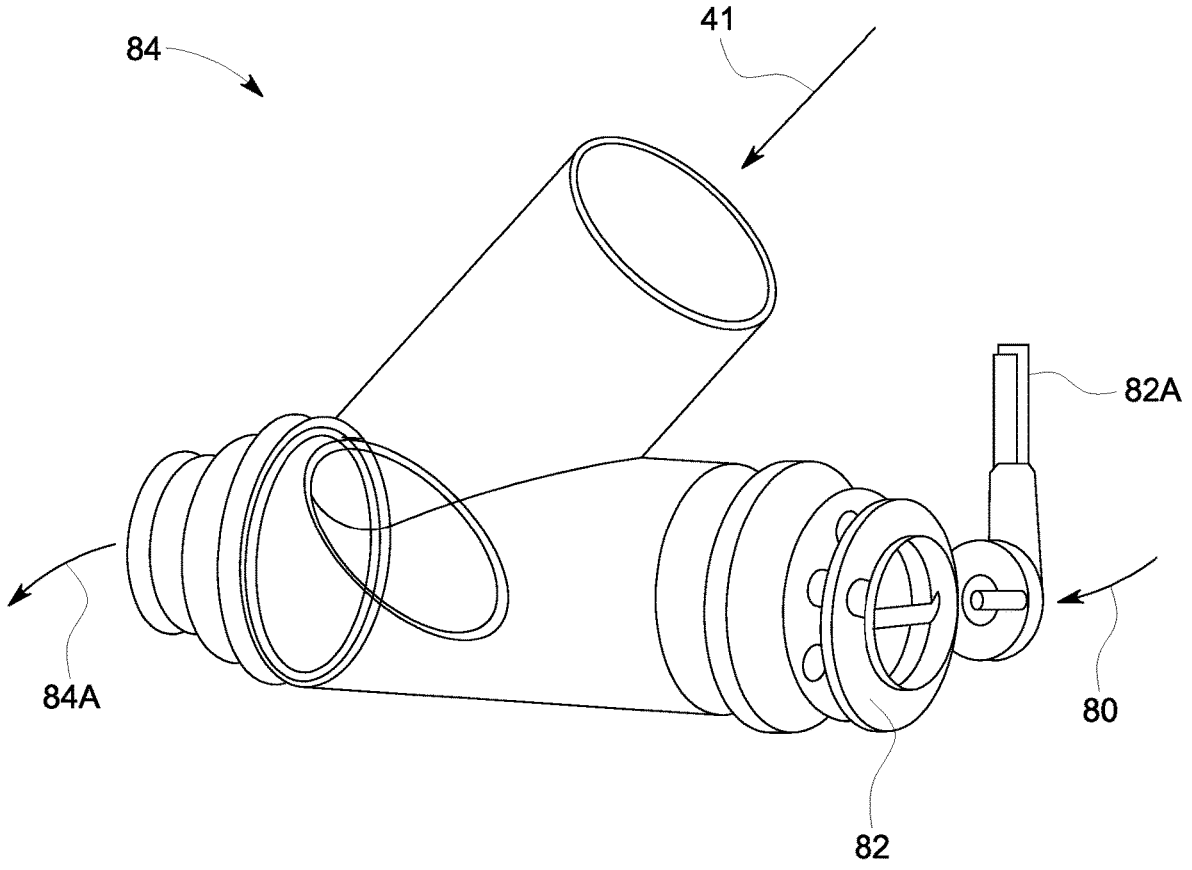
FIG. 7 is a detailed view of a system bypass lateral used in the odor control system of FIG. 1.

Referring to FIG. 7, along with FIG. 1, in some embodiments, fresh air enters through a treatment air admittance lateral 84 to combine with combined outflow 35 and/or demister outflow 41, where the combined outflow 84A therefrom moves toward media scrubber 70. As discussed above, the treatment air admittance lateral 84 can include a damper 82 that can be opened for maintenance of the media scrubber 70. In some embodiments, the damper 82 can be actuated with a damper handle 82A. In some embodiments, the damper 82 can be actuated remotely or automatically to periodically run a maintenance air flow through the media scrubber 70. In some embodiments, automatic maintenance can be performed when various sensors detect that no exhaust flow 12 is being received into the system 10, thus permitting automatic maintenance when odor treatment is not needed to be performed by the system 10.

In some embodiments, the system 10 includes an electronic sensor outside the media scrubber 70 that measures and indicates a gas being monitored. The electronic sensor can be used to monitor the exhaust outlet stream for contaminants which are indicative that the media 72 is spent. For example, in some embodiments, the system 10 includes an electronic sensor to detect gas breakthrough. The electronic sensor, can be, for example, but not limited to, a saturation indicator, or a saturation gauge, or a breakthrough saturation indicator. In some embodiments, the electronic sensor can monitor inlet gas and outlet gas.

Figure 8:
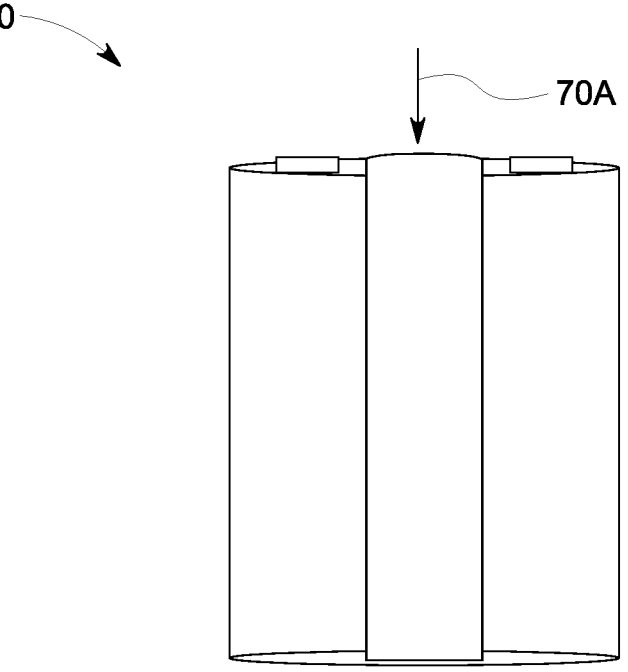
FIG. 8 is a side view of a radial scrubber used in the odor control system of FIG. 1.
Figure 9:
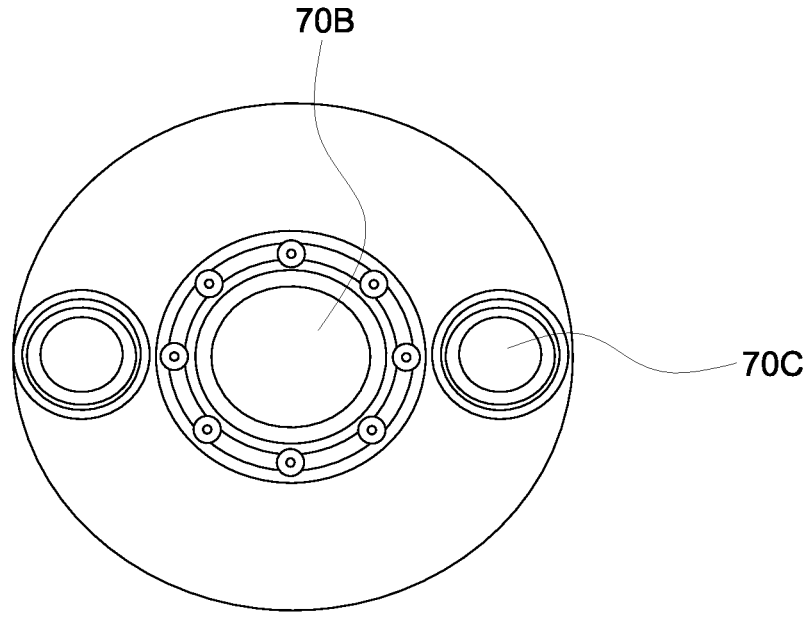
FIG. 9 is a top view of the radial scrubber of FIG. 8.
Figure 10:
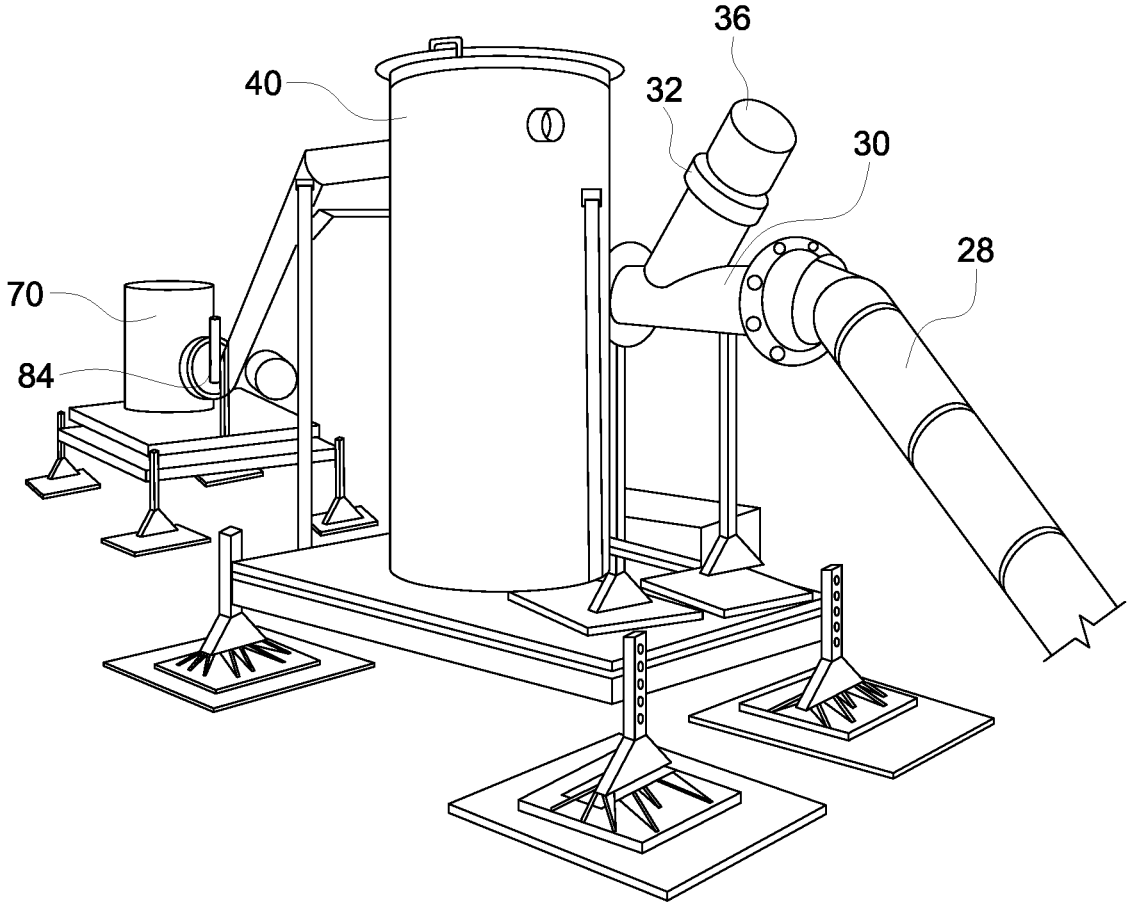
FIG. 10 is an exemplary installation, viewed from one side of the demister, of an odor control system according to an exemplary embodiment of the present invention.
Figure 11:
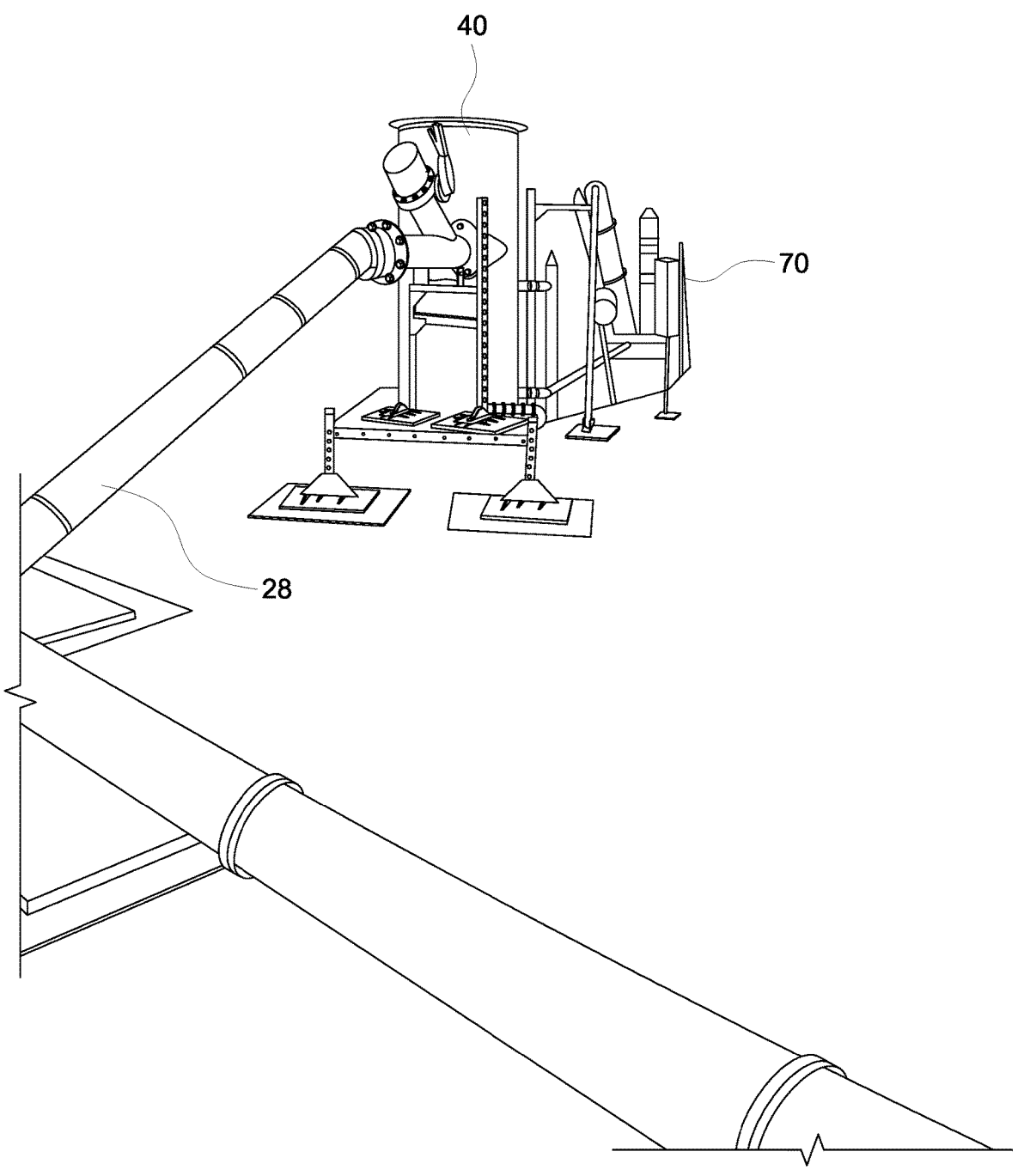
FIG. 11 is the exemplary installation of FIG. 10, viewed from the other side of the demister.
Figure 12:
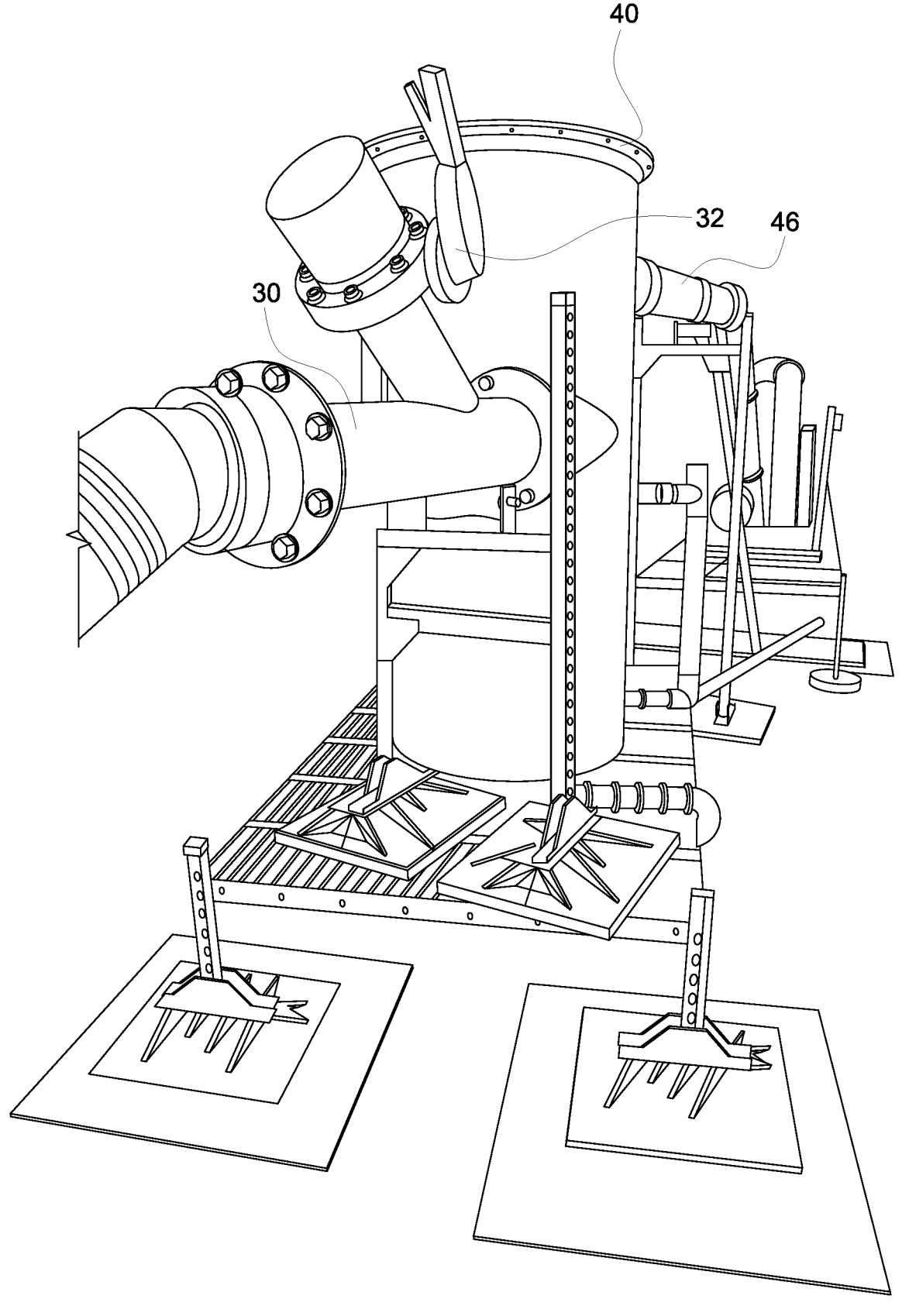
FIG. 12 is the exemplary installation of FIG. 10, viewed as a close up of the intake to the demister.
Figure 13:
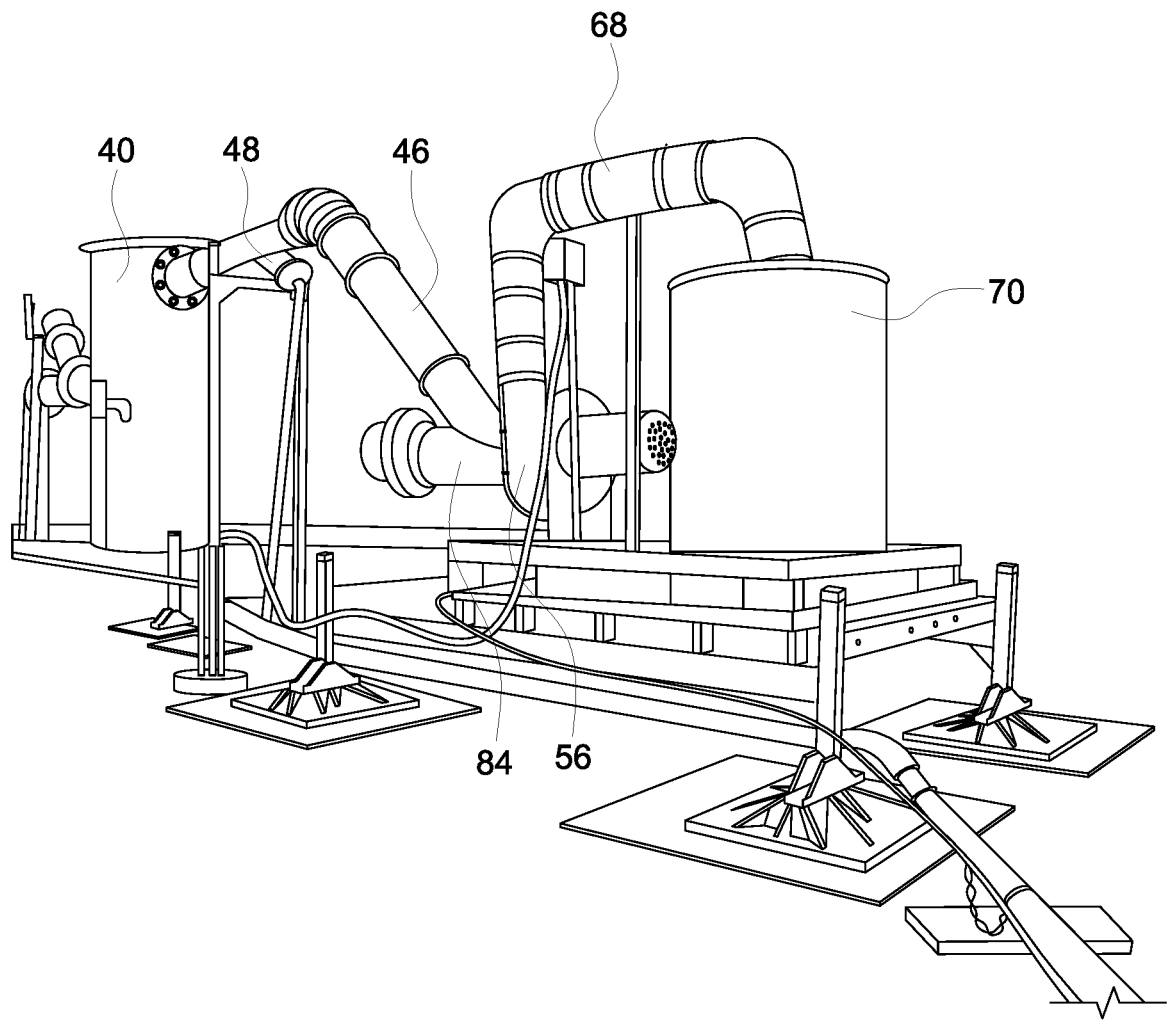
FIG. 13 is the exemplary installation of FIG. 10, viewed from the radial scrubber end thereof.

Referring to FIGS. 8 and 9, along with FIG. 1, in some embodiments, the media scrubber 70 receives an input flow 70A at an inlet 70B that is optionally pushed through the media scrubber 70 by a pressure blower 56, or pulled through the entire system 10, including media scrubber 70, in embodiments wherein pressure blower 56 is downstream of the media scrubber 70. In some embodiments, the media scrubber 70 includes one or more fill ports 70C. The fill ports 70C permit filling the media scrubber 70 with an adsorbent and/or an oxidizer media or removing spent media, for example. In some embodiments, the media scrubber 70 is a radial scrubber, such as, for example, but not limited to, an HRF-7 radial scrubber, produced by industrial odor control-.com.

FIGS. 10 through 13 illustrate an exemplary installation of the system 10 as described herein. In the embodiment shown, the system 10 is installed on a rooftop of a building and can be connected to one or more kettles and/or whirlpools, for example. It will be understood by those of ordinary skill in the art that depending on the system size and application, any number of kettles and/or whirlpools can provide an exhaust flow to the system 10.

Figure 14:
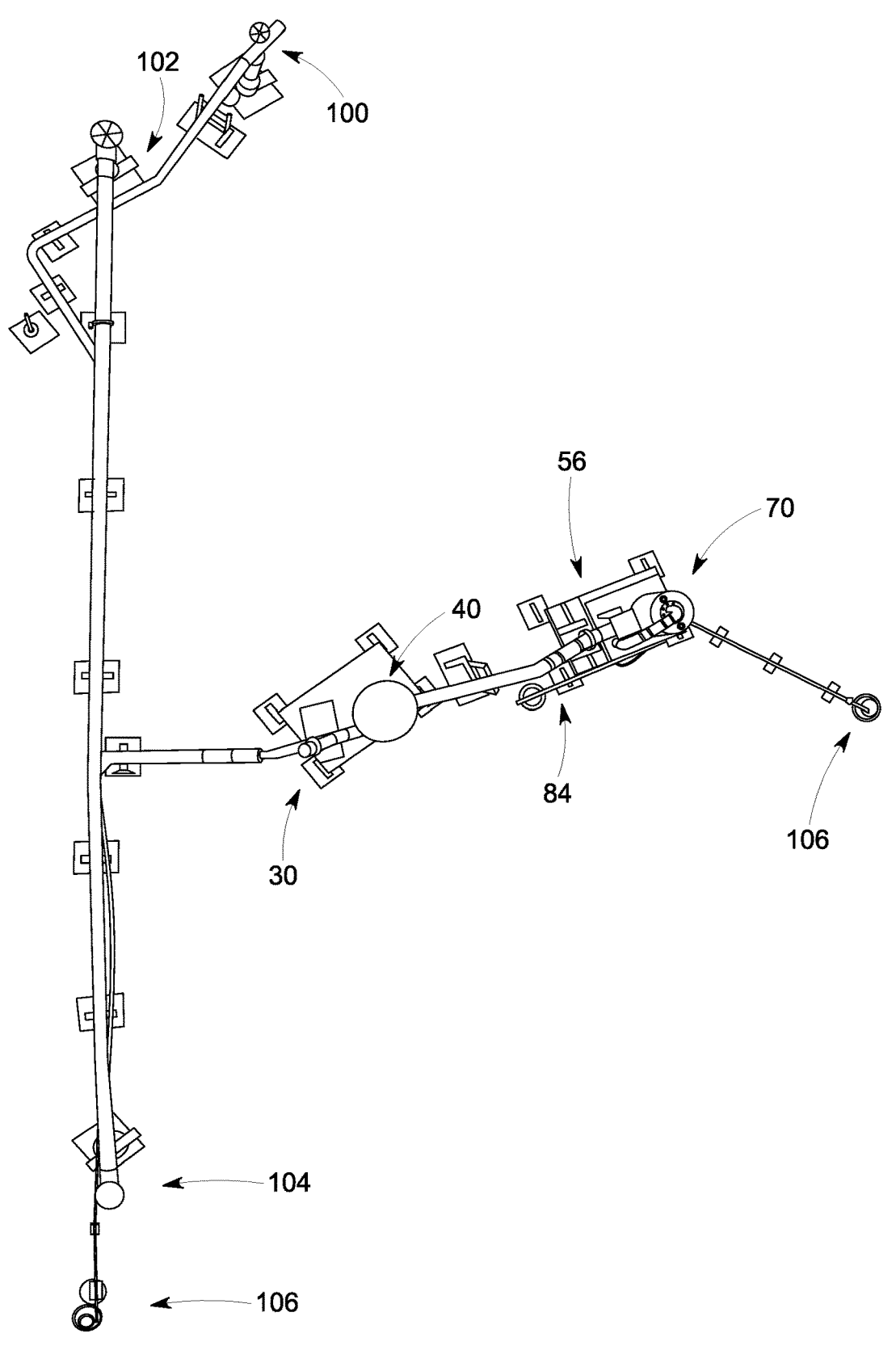
FIG. 14 is a plan view of the exemplary installation of FIG. 10.

FIG. 14 illustrates an exemplary arial view of the system 10 connected at two kettles and one whirlpool. In some embodiments, at the exhaust of whirlpool, a first air admittance tee 100 (similar to air admittance tee 14 described herein) is present. In some embodiments, at the exhaust of the first kettle, a second air admittance tee 102 (similar to air admittance tee 14 described above) is present. In some embodiments, at the exhaust of the second kettle, a third air admittance tee 104 (similar to air admittance tee 14 described above) is present. Thus, in some embodiments of the system described herein, each component (e.g., kettles and whirlpools) connected to the system has its own air admittance tee which initially dilutes and cools the exhaust flow. In some embodiments, one or more roof drains 106 receive flow via water drain lines 108 to drain condensed water created in the system 10.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

As is well known to those skilled in the art, many careful considerations and compromises typically must be made when designing for the optimal configuration of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

EXAMPLES

Example 1

An exhaust flow from two kettles was combined and treated in a system designed as described herein. Briefly, exhaust flow from the kettles was 216 degrees Fahrenheit (superheated and supersaturated) at the exhaust intake and contained between 15-23 ppm $H_2S$ and greater than 15 ppm DMS.

After being combined with fresh air flow, the combined flow in the intake pipe prior to reaching the air admittance lateral was lowered to 138 degrees Fahrenheit. Although dewpoint varies depending on outside temperature, the combined flow dropped below the dew point prior to entering the demister.

Condensed water was separated out in the demister and the combined flow exiting the demister was about 94 percent relative humidity.

The flow exiting from the media scrubber had undetectable levels of $H_2S$ and DMS, illustrating how a system as described herein can remove such contaminants from an exhaust stream.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. An odor control system comprising:
an air admittance tee operable to receive a superheated exhaust stream and a fresh air flow to create a combined outflow that is below the dew point;
at least one water drain configured to drain water from the system as it condenses in the system; and
a treatment zone operable to treat the combined outflow, wherein the treatment zone includes a media scrubber having an adsorbent media disposed therein.

2. The odor control system of claim 1, further comprising a demister downstream of the air admittance tee and a first pipe connecting the air admittance tee to the demister.

3. The odor control system of claim 2, wherein the at least one water drain is located in the first pipe.

4. The odor control system of claim 2, further comprising an air admittance lateral operable to permit an external air flow to move into the first pipe to mix with the combined outflow before entering the demister.

5. The odor control system of claim 4, further comprising a damper in the air admittance lateral for regulating an amount of the external air flow moving into the first pipe.

6. The odor control system of claim 1, further comprising:
a vent in the air admittance tee, the vent permitting escape of the exhaust flow therethrough without the exhaust flow moving through the odor control system; and
a valve in the vent, the valve operable to open and close the vent.

7. The odor control system of claim 6, wherein the valve of the air admittance tee is a barometric valve operable to regulate a volume of the air flow therethrough.

8. The odor control system of claim 1, wherein the treatment zone further includes an air admittance lateral having a damper operable to permit an external air flow to move through the treatment zone.

9. The odor control system of claim 8, further comprising a pressure gauge disposed on the media scrubber, the pressure gauge measuring a differential pressure through the media, wherein the differential pressure being above a predetermined limit indicates a need to open the damper of the air admittance lateral to permit the external air flow to dry the media.

10. The odor control system of claim 1, wherein the treatment zone includes a blower for facilitating air movement in the system.

11. The odor control system of claim 10, further comprising an air box disposed about the blower, wherein a vacuum is pulled through the air box during operation of the blower.

12. The odor control system of claim 1, wherein the at least one water drain is located in the treatment zone.

13. The odor control system of claim 1, further comprising one or more sensors disposed in the system, the one or more sensors operable to measure at least one of a fluid flow, a temperature and a relative humidity.

14. The odor control system of claim 1, wherein the adsorbent media comprises an activated carbon scrubber, ferric hydroxide impregnated clay, an iron sponge, or an impregnated media.

15. An odor control system comprising:

an air admittance tee operable to receive an exhaust flow;

a damper in the air admittance tee permitting an air flow to enter the air admittance tee and mix with the exhaust flow as the exhaust flow moves through the tee to create a combined outflow;

a first pipe connecting an outlet of the air admittance tee with a demister;

a first drain in the first pipe; and a second pipe connecting an outlet of the demister with a treatment zone, wherein the treatment zone comprises a media scrubber having an adsorbent material.

16. The odor control system of claim 15, further comprising:

a second water drain in the second pipe.

17. The odor control system of claim 15, further comprising:

a vent in the air admittance tee, the vent permitting escape of the exhaust flow therethrough without the exhaust flow moving through the odor control system; and a valve in the vent, the valve operable to open and close the vent.

18. The odor control system of claim 15, further comprising:

an air admittance lateral in the first or second pipe, wherein the air admittance lateral includes a damper operable to permit an external air flow to move into the to mix with the combined outflow before entering the demister or into the media scrubber.

19. The odor control system of claim 15, wherein the adsorbent media comprises activated carbon, ferric hydroxide impregnated clay, an iron sponge, or an impregnated media.

20. An odor control system comprising:

an air admittance tee operable to receive an exhaust flow;

a vent in the air admittance tee, the vent permitting escape of the exhaust flow therethrough without the exhaust flow moving through the odor control system;

a first valve in the vent, the valve operable to open and close the vent;

a first damper in the air admittance tee permitting a first external air flow to enter the air admittance tee and mix with the exhaust flow as the exhaust flow moves through the tee to create a combined outflow;

a first pipe connecting an outlet of the air admittance tee with a demister;

a first drain in the first pipe;

an air admittance lateral, communicating with the first pipe, operable to permit a second external air flow to move into the first pipe to mix with the combined outflow before entering the demister;

a second damper in the air admittance lateral operable to regulate a volume of the external air flow;

a media scrubber having an adsorbent material; and a pressure blower, wherein the pressure blower moves an outflow through the media scrubber.

* * * * *